United States Patent
Imai

(10) Patent No.: US 6,191,425 B1
(45) Date of Patent: Feb. 20, 2001

(54) MULTICOLOR FLUORESCENCE DETECTION TYPE ELECTROPHORETIC ANALYZER

(75) Inventor: Kazumichi Imai, Hitachinaka (JP)

(73) Assignee: Hatachi, Ltd., Tokyo (JP)

( * ) Notice: Under 35 U.S.C. 154(b), the term of this patent shall be extended for 0 days.

(21) Appl. No.: 09/023,561

(22) Filed: Feb. 13, 1998

(30) Foreign Application Priority Data

Feb. 18, 1997 (JP) .................................................. 9-034027

(51) Int. Cl.[7] .................................................. G01N 27/26
(52) U.S. Cl. .................................................. 250/458.1
(58) Field of Search .................................................. 250/458.1

(56) References Cited

U.S. PATENT DOCUMENTS

| | | | |
|---|---|---|---|
| 5,062,942 | 11/1991 | Kambara et al. | 204/299 |
| 5,162,654 | 11/1992 | Kostichka et al. | 250/458.1 |
| 5,274,240 * | 12/1993 | Mathies et al. | 250/458.1 |
| 5,439,578 | 8/1995 | Dovichi et al. | 204/299 |
| 5,516,409 * | 5/1996 | Kambara | 250/458.1 |
| 5,529,679 | 6/1996 | Takahashi et al. | 204/603 |
| 5,534,703 * | 7/1996 | Kambara et al. | 250/458.1 |
| 5,582,705 | 12/1996 | Yeung et al. | 204/603 |
| 5,667,656 * | 9/1997 | Kambara | 250/458.1 |
| 5,730,850 * | 3/1998 | Kambara et al. | 204/603 |
| 5,780,857 * | 7/1998 | Harju et al. | 250/458.1 |
| 5,790,727 | 8/1998 | Dhadwal et al. | 385/38 |

FOREIGN PATENT DOCUMENTS

| | | |
|---|---|---|
| 1116441 | 5/1989 | (JP) . |
| 1148946A | 6/1989 | (JP) . |
| 2269936 | 11/1990 | (JP) . |
| 2269937 | 11/1990 | (JP) . |
| 795033B2 | 10/1995 | (JP) . |

* cited by examiner

Primary Examiner—Constantine Hannaher
Assistant Examiner—Oti'lia Gabor
(74) Attorney, Agent, or Firm—Kenyon & Kenyon

(57) ABSTRACT

A plurality of samples are separated into sample components by means of electrophoresis in a plurality of capillaries. Light is radiated onto the separated sample components. Fluorescence emitted from the sample components is measured by a detector unit. In the detector unit, the fluorescence from the sample components is collected by a lens, filtered by a filter set to select light of predetermined wavelengths, split into four bundle of rays by right-angle prisms, and focussed on four linear array sensors so as to be detected.

10 Claims, 7 Drawing Sheets

LASER BEAM

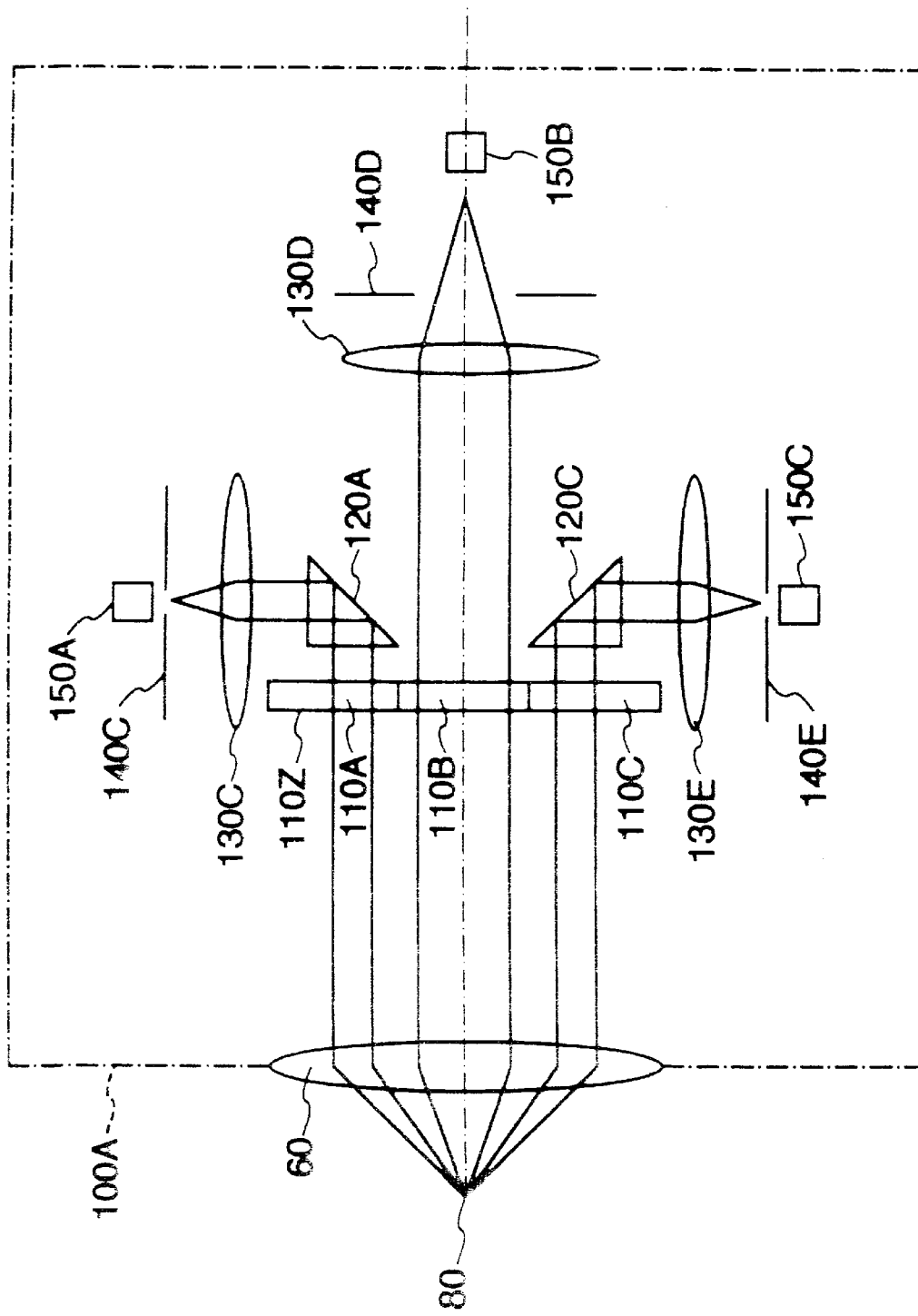

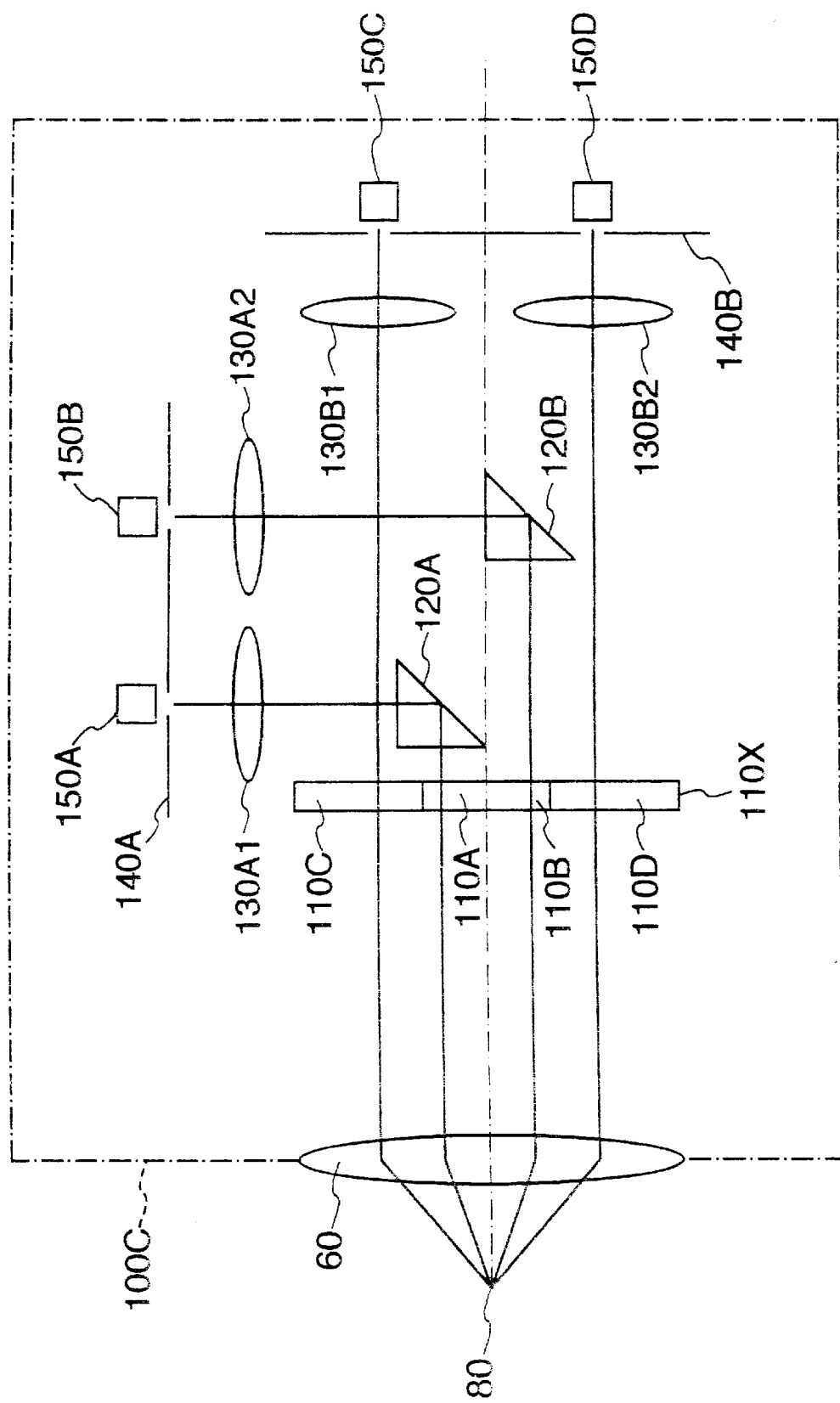

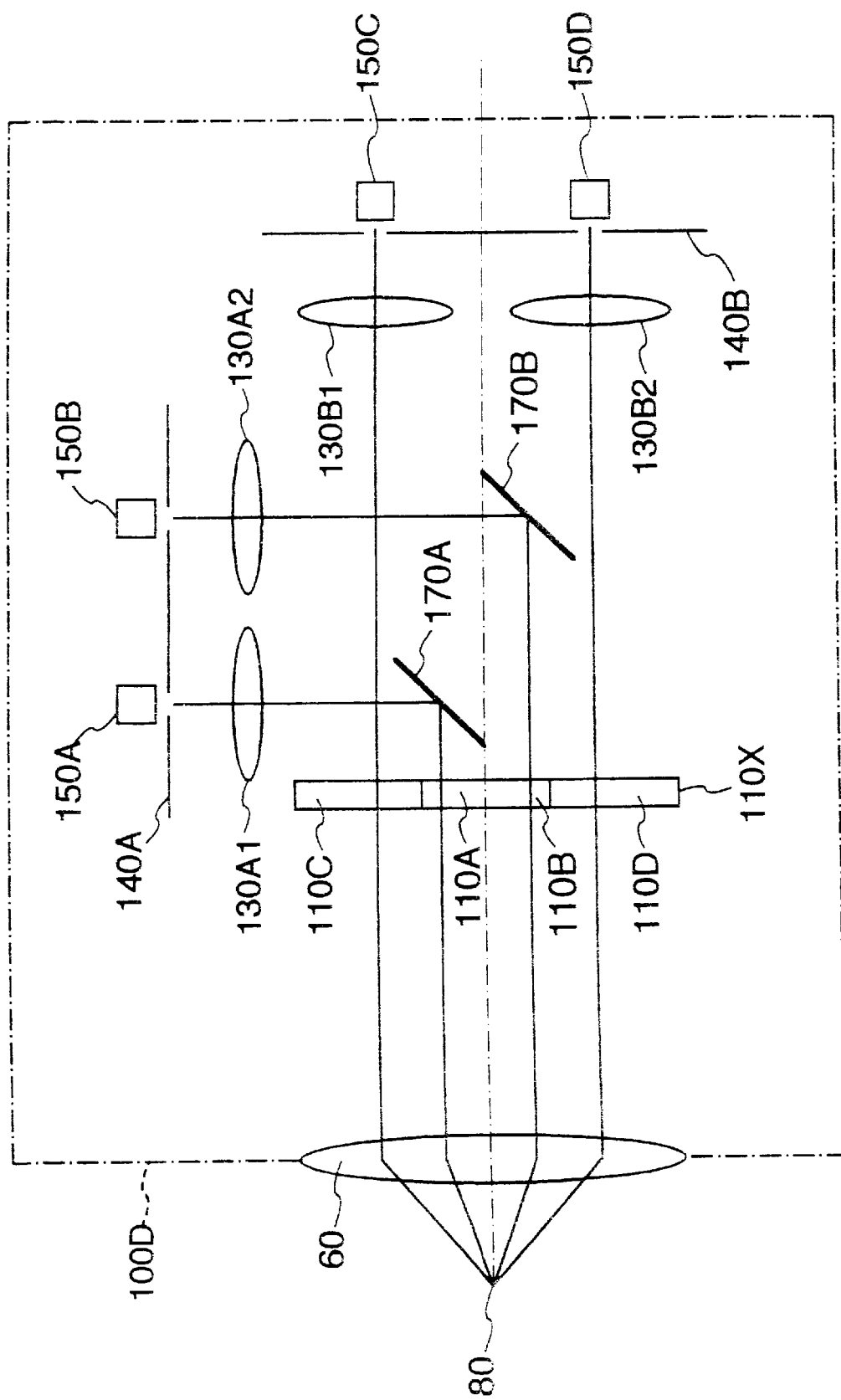

MULTICOLOR FLUORESCENCE DETECTION TYPE ELECTROPHORETIC ANALYZER

BACKGROUND OF THE INVENTION

The present invention relates to a multicolor fluorescence detection type electrophoretic analyzer, and particularly relates to a multicolor fluorescence detection type electrophoretic analyzer adapted to a DNA sequencer using a plurality of capillaries or a plurality of fine channels as separation media for analyzing biological samples such as DNA (deoxyribonucleic acid), etc.

DNA analyzing techniques based on electrophoresis, particularly DNA sequencers, have become popular. With the increase of the needs of DNA analysis, analyzing throughput has been required to be enhanced.

One method for enhancing analyzing throughput is integration of separation media for simultaneous analysis of a plurality of samples. One conventional technique is a DNA sequencer in which thin-layer gel formed between two flat glass plates is used as a separation medium. In the DNA sequencer, a large number of samples are subjected to electrophoresis so that the samples are arranged side by side between two flat glass plates from one side to the opposite side. Therefore, a sufficient distance is required to be taken between migration lanes so that adjacent samples are not mixed in the lanes. Accordingly, the density of integration of separation media is limited.

On the other hand, a DNA sequencer in which capillaries each having a fine inner diameter are disposed parallelly to each other so that different samples are subjected to electrophoresis in the capillaries respectively to thereby enhance the degree of integration has been proposed as another conventional technique for integrating separation media. In the proposed technique, because the sectional areas of the lanes are reduced compared with the DNA sequencer using flat glass plates, the current due to the electrophoresis is reduced so that the generation of Joule heat can be suppressed. Accordingly, a higher electrophoresis voltage than the conventional voltage can be applied so that the samples migrate at a high speed. Further, a method in which fine grooves as migration lanes are formed in a surface of a glass plate has been also discussed. The discussed method is effective for enhancing the degree of integration of migration lanes.

Further, integration of detection systems is required for enhancing the throughput of analyzing. That is, methods for measuring a plurality of migration lanes simultaneously and measuring a plurality of wavelengths corresponding to a plurality of fluorophores simultaneously have been described, for example, in U.S. Pat. No. 5,062,942, U.S. Pat. No. 5,162,654, JP-A-2-269937, JP-A-2-269936, JP-A-1-116441, JP-A-1-148946 and JP-B-7-95033. In each of those methods, a two-dimensional charge coupled device (CCD) is used so that detection wavelengths and images of migration lanes are evolved and focussed in two-dimensional directions on a detector surface so that one axis corresponds to the detection wavelengths and the other axis corresponds to the images.

Because the two-dimensional CCD evolves and focuses the plurality of detection wavelengths and the plurality of images (positional information) of migration lanes in two-dimensional directions respectively on the surface of the detector, analytically unnecessary information is measured by a large number of devices on the surface of the detector. Practically, unnecessary portions must be, however, removed by signal processing so that only useful portions are used selectively because necessary information concerning wavelengths and positions is present only in a slight portion. Because a large detector, however, has a large number of devices on its surface, both signal transferring and signal processing are so complex that a large time is generally required for the signal transferring and signal processing. Furthermore, the devices per se are so expensive that the cost of the devices inclusive of circuits for performing the signal transferring and signal processing at a high speed increases.

If linear array sensors can be used as detection devices in necessary positions, not only the system can be configured relatively inexpensively but also measurement can be performed in necessary portions limitedly. Accordingly, there is a possibility that data transferring and data processing are made speedily and simply.

Therefore, the present inventor has examined that a plurality of linear array sensors are disposed in a plane so as to be substantially equivalent to the two-dimensional sensor so that two-dimensionally evolved images are detected by such linear array sensors to thereby simplify signal processing. When the linear array sensors each having a light-receiving surface which per se is small in external size of about 30 mm×0.5 mm are mounted on a substrate, the external size is, however, enlarged to about 50 mm×50 mm. It is therefore difficult to realize the configuration in which the linear array sensors are disposed in a plane. Even in the case where images of the plurality of migration lanes are distributed into light paths by a polygonal prism, the distance between focussed spots is limited to a range of from about 5 mm to 8 mm at the maximum. This is because the detector has a large external size of about 50 mm×50 mm so that the distance between each migration lane and a corresponding lens of the detector must be taken large. Accordingly, the quantity of fluorescence taken in the detector through the lens among fluorescence radially diffused from the migration lanes is reduced so as to be inversely proportional to the square of the distance. Consequently, detecting sensitivity is reduced.

A DNA sequencer in which fluorescence from a plurality of migration lanes is detected simultaneously without use of any two-dimensional sensor is disclosed in U.S. Pat. No. 5,439,578. According to the U.S. Pat. No. 5,439,578, fluorescence emitted from a plurality of capillaries disposed parallelly to each other is introduced into optical fibers through condenser lenses and filters, and light is made incident from the optical fibers to photo detectors so as to be detected by the photo detectors.

SUMMARY OF THE INVENTION

An object of the present invention is to provide a multicolor fluorescence detection type electrophoretic analyzer which uses a plurality of linear array sensors so that fluorescence emitted from a plurality of migration lanes can be detected simultaneously at high sensitivity.

In order to achieve the foregoing object, according to the present invention, provided is a multicolor fluorescence detection type electrophoretic analyzer for separating a plurality of samples in a plurality of migration lanes by means of electrophoresis, radiating light onto the thus separated sample components and measuring fluorescence emitted from the sample components by means of a detector unit including a linear array sensor, wherein the detector unit includes a light collection means for collecting the fluorescence into a bundle of rays, a luminous flux splitter means for splitting the bundle of rays collected by the light collection means into a plurality of bundle of rays, the linear array sensors for detecting light of the bundle of rays split by the luminous flux splitter means, and a wavelength selection means arranged between the light collection means and the linear array sensors for selecting light of different wavelengths corresponding to the split bundle of rays.

In such a configuration, detecting sensitivity can be enhanced as the linear array sensors are used as a detection system.

Preferably, the luminous flux splitter means is constituted by a plurality of right-angle prisms arranged in the light path of the bundle of rays collected by the light collection means for reflecting a part of the bundle of rays perpendicularly. In such a configuration, optical axes can be made coincident with each other easily so that the system can be produced easily.

Preferably, the luminous flux splitter means is constituted by dichroic mirrors arranged in the light path of the bundle of rays collected by the light collection means for reflecting light of predetermined wavelengths in the bundle of rays but transmitting light of the other wavelengths. In such a configuration, not only the number of constituent parts can be reduced but also the size of the system can be reduced.

Preferably, the luminous flux splitter means is constituted by a plurality of mirrors arranged in the light path of the bundle of rays collected by the light collection means for reflecting a part of the bundle of rays. In such a configuration, not only the number of constituent parts can be reduced but also the size of the system can be reduced.

BRIEF DESCRIPTION OF THE DRAWINGS

FIG. 4 is a configuration diagram of an optical system showing the detector unit used in the multicolor fluorescence detection type electrophoretic analyzer according to a second embodiment of the present invention;

FIG. 6 is a configuration diagram of an optical system showing the detector unit used in the multicolor fluorescence detection type electrophoretic analyzer according to a fourth embodiment of the present invention; and FIG. 7 is a configuration diagram of an optical system showing the detector unit used in the multicolor fluorescence detection type electrophoretic analyzer according to a fifth embodiment of the present invention.

DESCRIPTION OF THE PREFERRED EMBODIMENTS

Figure 1:
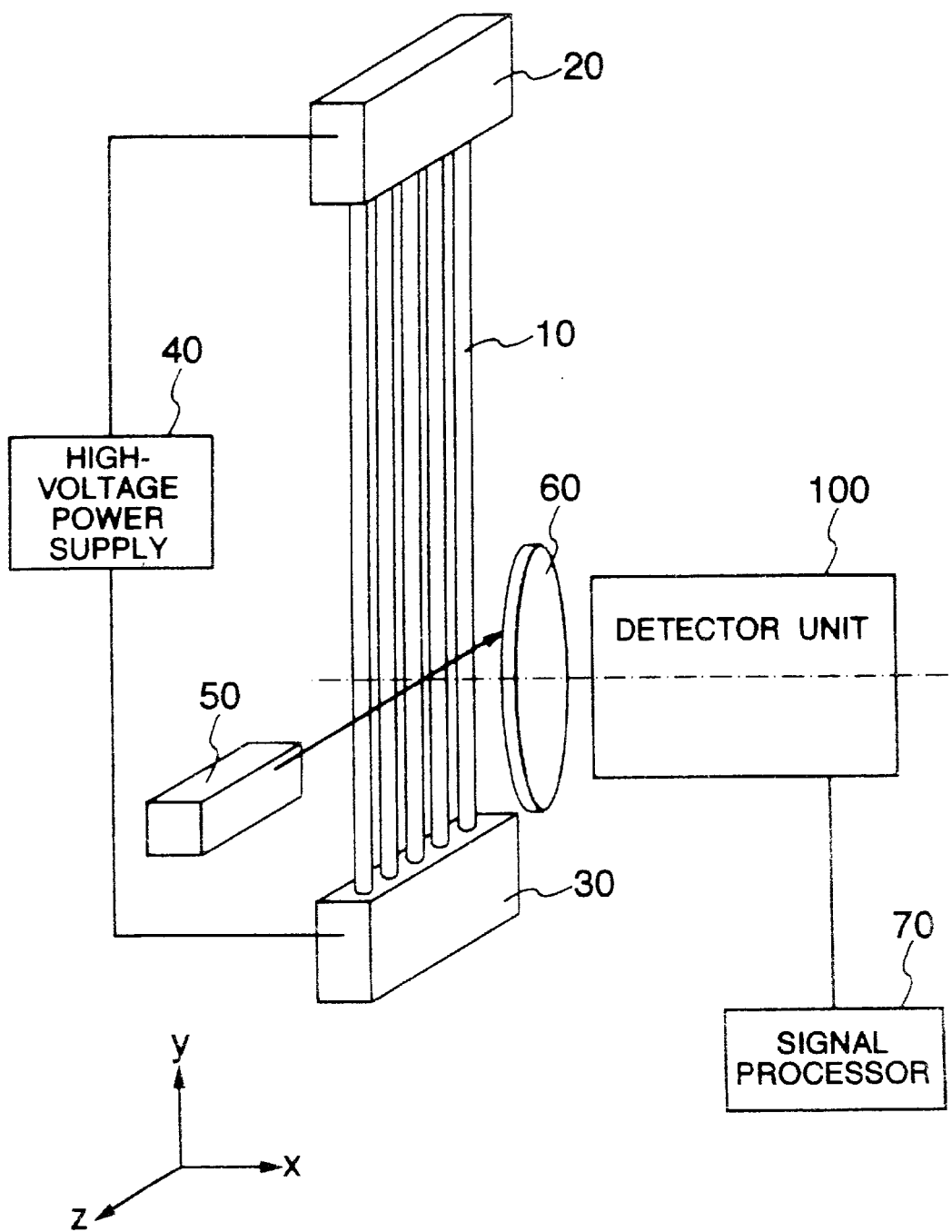
FIG. 1 is an explanatory diagram showing the overall configuration of a multicolor fluorescence detection type electrophoretic analyzer according to an embodiment of the present invention.
Figure 2:
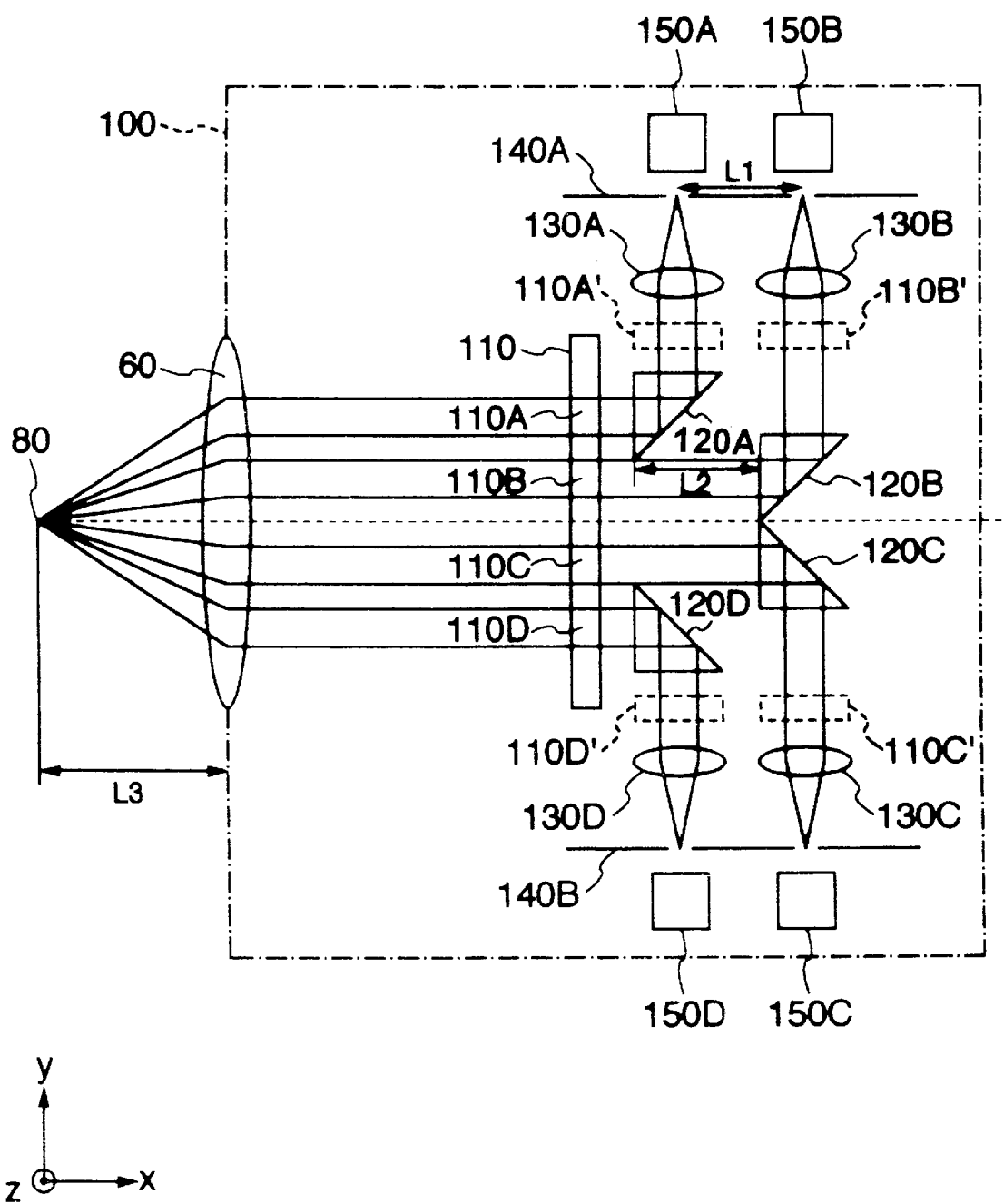
FIG. 2 is a configuration diagram of an optical system showing a detector unit used in the multicolor fluorescence detection type electrophoretic analyzer according to the embodiment of the present invention.

Referring to FIGS. 1 through 3, a multicolor fluorescence detection type electrophoretic analyzer according to an embodiment of the present invention will be described below. FIG. 1 is an explanatory diagram showing the overall configuration of the multicolor fluorescence detection type electrophoretic analyzer according to the embodiment of the present invention.

A plurality of capillaries 10 are disposed parallelly to each other and filled with separation gel matrices. Opposite ends of the capillaries 10 are connected to buffers (solution electrolytes) 20 and 30. Samples to be measured are introduced into the capillaries 10 from the buffer 20 side. A high-voltage power supply 40 is used to apply an electrophoresis voltage between the buffers 20 and 30. In the case where the samples to be measured are nucleic acid samples, fluorescent dyes having different fluorescent characteristics corresponding to terminal bases of the samples respectively are connected to the terminal bases of the samples in advance by a reaction operation. When the samples introduced into the capillaries 10 respectively from the buffer 20 side move in the capillaries 10, the samples are separated into components by the difference of mobility mainly based on the difference of molecular weight.

At respective electrophoretic ends of the capillaries 10 near the buffer 30, light from a laser 50 is radiated to the separated samples so that the light passes through all the capillaries. As a result, the fluorescent dyes connected to the terminal bases emit fluorescence. The fluorescence emitted from the respective sample components are collected by a condenser lens 60 and introduced, as a collimated bundle of rays, into a detector unit 100. In the detector unit 100, the collimated bundle of rays is separated into respective wavelength components to be detected. The respective wavelength components are detected by the detector unit 100. The condenser lens 60 is a constituent member of the detector unit 100. In FIG. 1, the condenser lens 60 is shown separately in order to clarify the state in which the fluorescence emitted from the respective sample components is introduced into the detector unit 100. Signals obtained by the detector unit 100 are delivered to a signal processor 70. In the signal processor 70, the signals are processed so that not only the terminal bases of the samples are identified on the basis of the wavelength of the fluorescence but also the base sequences of the nucleic acid samples are analyzed on the basis of the measured signals.

Although the above description has been made about the case where samples are introduced into capillaries respectively from the buffer 20, the present invention can be also applied to the case where samples are introduced into capillaries respectively reversely from the buffer 30. In this case, the electrodes of the high-voltage power supply 40 are reversed to each other, and the laser 50 is disposed near the buffer 20.

In analysis for determining the base sequence of DNA, four wavelengths corresponding to fluorescent dyes are generally used for measurement because DNA generally has four kinds of bases disposed in a regular sequence and because four kinds of fluorescent dyes are connected to the four kinds of terminal bases.

In FIG. 1, the Y-axis direction is assumed to be the direction of extension of the capillaries 10, and the X-axis direction is assumed to be the direction of arrangement of the lens 60 and the detector unit 100.

Referring to FIG. 2, the configuration of the detector unit in this embodiment will be described below.

FIG. 2 is a configuration diagram of an optical system showing the configuration of the detector unit used in the multicolor fluorescence detection type electrophoretic analyzer according to the embodiment of the present invention.

Fluorescence from light-emitting points 80 is collected by the lens 60. The light-emitting points 80 are a plurality of points at which fluorescence is emitted when light from the laser 50 is radiated onto the samples separated by the capillaries 10 shown in FIG. 1. Although FIG. 2 shows the case where the lens 60 is constituted by a single lens, the lens 60 may be constituted by a plurality of lenses. When the light-emitting points 80 and the lens 60 are arranged so that the light-emitting points 80 are located in the focal position of the lens 60, light collected by the lens 60 becomes a collimated bundle of rays to be led to the detector unit 100.

For correlation with FIG. 1, the Y-axis direction is assumed to be the direction of extension of the capillaries 10, and the X-axis direction is assumed to be the direction of the light axis of the bundle of rays collimated by the lens 60. As shown in FIG. 1, the plurality of capillaries, for example, five capillaries 10 are assumed to be disposed in parallel with the Z-axis direction perpendicular to the plane of paper, that is, perpendicular to the X- and Y-axis directions.

The detector unit 100 includes a filter set 110, right-angle prisms 120A to 120D, lenses 130A to 130D, spacial filters (slits) 140A and 140B, and four linear array sensors 150A to 150D.

The filter set 110 has band-pass filters 110A, 110B, 110C and 110D for selecting four kinds of light having different wavelengths. The filter 110A selects light of a first wavelength λ1, for example, 500 nm. The filter 110B selects light of a third wavelength λ3, for example, 540 nm. The filter 110C selects light of a second wavelength λ2, for example, 520 nm. The filter 110D selects light of a fourth wavelength λ4, for example, 560 nm.

After passing through the filter set 110, the bundle of rays is bent perpendicularly by the four right-angle prisms 120A, 120B, 120C and 120D respectively so as to be split into four bundle of rays. That is, the optical system in this embodiment is designed so that one bundle of rays is split into four bundle of rays. Contrariwise, the conventional polygonal prism is designed so that the light path is changed correspondingly to the wavelength.

The four bundle of rays are converged by the lenses 130A, 130B, 130C and 130D so as to be focussed on light-receiving surfaces of the linear array sensors 150A, 150B, 150C and 150D respectively. That is, after four kinds of light of different wavelengths are selected by the filters 110A to 110D, the light emitted from the plurality of light-emitting points 80 is focussed on the four linear array sensors 150A to 150D so that the fluorescent intensity corresponding to the four kinds of wavelengths is detected for every capillary by the four linear array sensors respectively. When, for example, five capillaries 10 are disposed parallelly to each other, each of the linear array sensors 150A to 150D has five light-receiving surfaces. The five light-receiving surfaces are arranged in the Z-axis direction (perpendicular to the plane of paper, that is, perpendicular to the X- and Y-axis directions). Accordingly, after the four kinds of light of different wavelengths are selected by the filters 110A to 110D, the fluorescent intensity corresponding to the four kinds of wavelengths of the light emitted from five light-emitting points in the five capillaries 10 is detected by the five light-receiving surfaces of the four linear array sensors 150A to 150D, respectively.

The spacial filters (slits) 140A and 140B are arranged between the lenses 130A, 130B, 130C and 130D and the linear array sensors 150A, 150B, 150C and 150D so that stray light is prevented. Further, shades may be disposed between adjacent ones of the four bundle of rays so that light is prevented from leaking to each other.

Figure 3A:
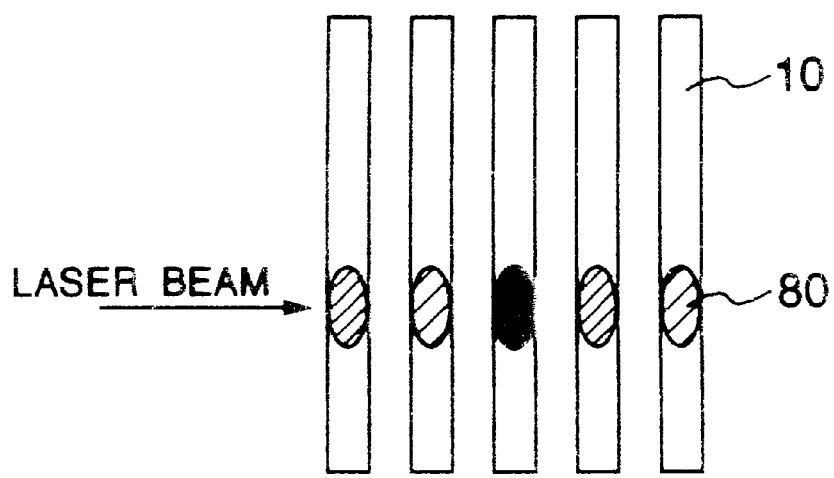
FIGS. 3A and 3B are explanatory diagrams showing light-emitting points and images focussed on light-receiving surfaces of linear array sensors in the multicolor fluorescence detection type electrophoretic analyzer according to the embodiment of the present invention.
Figure 3B:
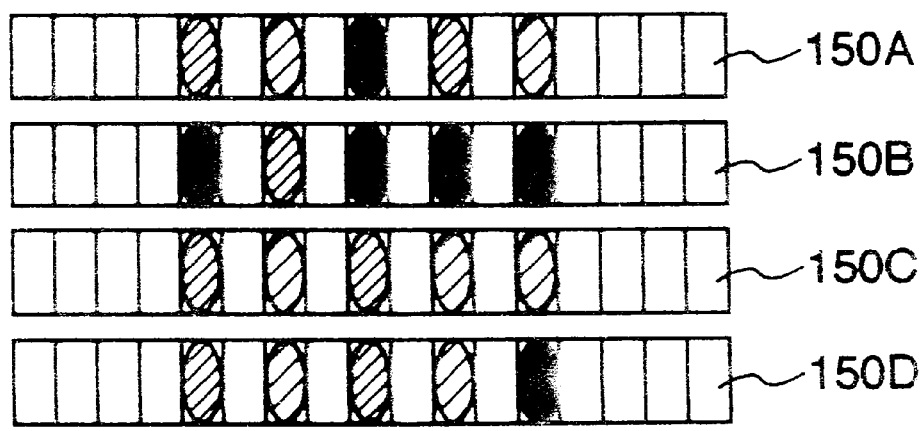

Referring to FIGS. 3A and 3B, relations between light-emitting points and images focussed on the light-receiving surfaces of the linear array sensors in this embodiment will be described below.

FIG. 3A shows states of light-emitting points. When light from the laser is radiated onto the separated samples in five capillaries 10, five points 80 at which fluorescence is emitted are formed.

FIG. 3B shows the images of the light-emitting points 80 focussed on the light-receiving surfaces of the linear array sensors 150A to 150D. The images focussed on the light-receiving surfaces of the linear array sensors 150A to 150D are images corresponding to light of different wavelengths respectively.

In the case where a two-dimensional charge coupled device is used, only regions in which images are formed are required among all the detection surfaces. Accordingly, other regions which form the background of the images must be selected or removed. Accordingly, a long time is required for transferring data and selecting data, so that the resulting circuit becomes too complex to obtain high-speed processing.

Contrariwise, in this embodiment, only necessary images are focussed on the light-receiving surfaces of the linear array sensors 150A to 150D so that necessary information can be used as detection signals directly. Accordingly, in this embodiment, processing can be simplified.

As described above, in this embodiment, a bundle of rays is split by the four right-angle prisms 120A to 120D. The distance L1 between the linear array sensors 150A and 150B is selected to be sufficiently large. Assuming that the size of the detector unit in which the linear array sensors are arranged on a substrate is 50 mm, then the distance L1 needs to be about 50 mm. In this embodiment, because the collimated bundle of rays is split by the right-angle prisms arranged in the collimated bundle of rays so that the distance L2 can be changed freely, it is easy to widen the distance L2 between the right-angle prisms 120A and 120B to about 50 mm.

Further, in this embodiment, four kinds of light of different wavelengths are measured simultaneously by one detector unit 100. Because the distance L3 between the lens 60 and each light-emitting point 80 can be shortened easily by the reduction of the focal length of the lens 60, the solid angle at which light of the light-emitting point 80 is taken into the detector unit 100 can be widened so that detecting sensitivity can be improved.

Further, right-angle prisms 120A to 120D are used as means for splitting the bundle of rays. One side of each of the right-angle prisms 120A to 120D is placed on an optical base having a smooth plane so as to be able to slide it in the X-axis direction to form the images on the linear array sensors, as a result, it becomes easy to assemble the device.

Although the above description has been made about the case where filters 110A to 110D are arranged between the lens 60 and the right-angle prisms 120A to 120D, the invention may be applied also to the case where such filters 110 are arranged in the collimated bundle of rays between the right-angle prisms 120A to 120D and the lenses 130A to 130D as represented by the broken line. Alternatively, such a filter set 110 may be arranged in the collimated bundle of rays between the lenses 130A to 130D and the spacial filters 140A and 140B.

Although the above description has been made about the case where light emitted from the light-emitting point 80 is collimated in the form of a collimated bundle of rays by the lens 60, the invention may be applied also to the case where light emitted from the light-emitting point 80 is converged in the form of a nearly collimated but converged bundle of rays by the lens 60. The right-angle prisms 120A to 120D may be replaced by flat mirrors.

Further, the spacial filters (slits) may be inserted in the front or rear of the lenses 130A to 130D or in the front or rear of the right-angle prisms 120A to 120D if necessary.

In the aforementioned embodiment, not only linear array sensors can be used as a detection system in the multicolor fluorescence detection type electrophoretic analyzer but also detecting sensitivity can be enhanced.

FIG. 4 is a configuration diagram of an optical system showing the configuration of the detector unit used in the multicolor fluorescence detection type electrophoretic analyzer according to a second embodiment of the present invention. The overall configuration of the multicolor fluorescence detection type electrophoretic analyzer according to this embodiment is the same as shown in FIG. 1.

Fluorescence emitted from the light-emitting point 80 is collected by the lens 60. Although FIG. 4 shows the case where, with respect to the light-emitting point 80, the lens 60 is constituted by one lens, the invention can be applied also to the case where the lens 60 is constituted by a plurality of lenses. When the light-emitting point 80 is located in the focal position of the lens 60, light collected by the lens 60 forms a collimated bundle of rays to be led to the detector unit 100A.

The detector unit 100A includes a filter set 110Z, right-angle prisms 120A and 120C, lenses 130C to 130E, spacial filters (slits) 140C to 140E, and three linear array sensors 150A to 150C.

The filter set 110Z has band-pass filters 110A, 110B and 110C for selecting three kinds of light of different wavelengths. The filter 110A selects light of a first wavelength $\lambda 1$, for example, 500 nm. The filter 110B selects light of a third wavelength $\lambda 3$, for example, 540 nm. The filter 110C selects light of a second wave-length $\lambda 2$, for example, 520 nm.

After passing through the filter set 110Z, the bundle of rays is bent perpendicularly by the two right-angle prisms 120A and 120C. The residual part of the bundle of rays moves straight and is split into three bundle of rays. That is, the optical system in this embodiment is designed so that one bundle of rays is split into three bundle of rays.

The three bundle of rays are converged by the lenses 130C to 130E so as to be focussed on light-receiving surfaces of the linear array sensors 150A, 150B and 150C respectively. That is, after light emitted from the plurality of light-emitting points 80 passes through the filters 110A to 110C so that three kinds of light of different wavelengths are selected by the filters 110A to 110C, fluorescence intensity corresponding to the three kinds of wavelengths is detected by the three linear array sensors 150A to 150C respectively.

As shown in this embodiment, the present invention can be applied also to the three-wavelength detection type optical system. Because one bundle of rays is split into three different directions, the three linear array sensors can be arranged in different positions. Accordingly, because there is no interference among the three linear array sensors, the detector unit having the linear array sensors arranged therein can be arranged easily even in the case where the detector unit is large.

The other features and modifications are equivalent to those in the first embodiment shown in FIG. 2.

Figure 5:
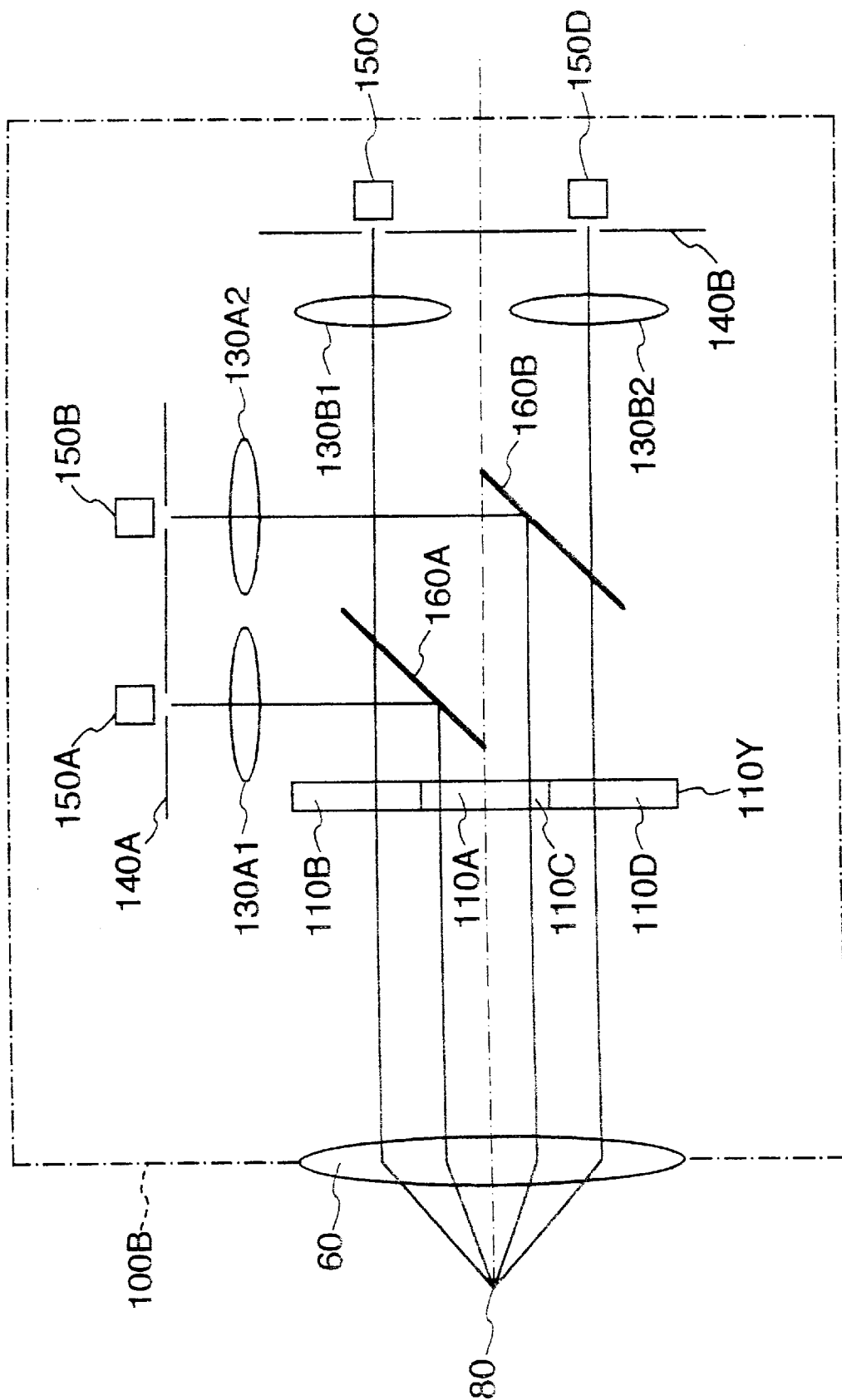
FIG. 5 is a configuration diagram of an optical system showing the detector unit used in the multicolor fluorescence detection type electrophoretic analyzer according to a third embodiment of the present invention.

FIG. 5 is a block diagram of an optical system showing the configuration of the detector unit used in the multicolor fluorescence detection type electrophoretic analyzer according to a third embodiment of the present invention. The overall configuration of the multicolor fluorescence detection type electrophoretic analyzer according to this embodiment is the same as shown in FIG. 1.

Fluorescence emitted from each light-emitting point 80 is collected by the lens 60. Although FIG. 5 shows the case where the lens 60 is constituted by a single lens, the invention can be applied also to the case where the lens 60 is constituted by a plurality of lenses. When the light-emitting point 80 is located in the focal position of the lens 60, light collected by the lens 60 forms a collimated bundle of rays to be led to the detector unit 100B.

The detector unit 100B includes a filter set 110Y, dichroic mirrors 160A and 160B, lenses 130A1, 130A2, 130B1 and 130B2, spacial filters (slits) 140A and 140B, and four linear array sensors 150A to 150D.

The filter set 110Y has band-pass filters 110A, 110B, 110C and 110D for selecting four kinds of light of different wavelengths like FIG. 2.

After passing through the filter set 110Y, the bundle of rays enters into the dichroic mirrors 160A and 160B. Each of the dichroic mirrors has different reflecting/transmitting characteristic correspondingly to the wavelength component so that the dichroic mirror reflects light of a wavelength shorter than the predetermined wavelength and transmits light of a wavelength larger than a predetermined wavelength. Accordingly, the bundle of rays can be split into two bundle of rays by one dichroic mirror so that the predetermined wavelength becomes a boundary between the two bundle of rays.

Light of the wavelength $\lambda 1$ selected by the filter 110A is reflected and bent perpendicularly by the dichroic mirror 160A whereas light of the wavelength $\lambda 2$ selected by the filter 110B passes through the dichroic mirror 160A. Further, light of the wavelength $\lambda 3$ selected by the filter 110C is reflected and bent perpendicularly by the dichroic mirror 160B whereas light of the wavelength $\lambda 4$ selected by the filter 110D passes through the dichroic mirror 160B. As described above, the optical system in this embodiment is designed so that one bundle of rays is split into four bundle of rays.

The four bundle of rays are converged by the lenses 130A1, 130A2, 130B1 and 130B2 are focussed on light-receiving surfaces of the linear array sensors 150A to 150D respectively. That is, after light emitted from the plurality of light-emitting points 80 passes through the filters 110A to 110D so that four kinds of light of different wavelengths are selected by the filters 110A to 110D, fluorescence intensity corresponding to the four kinds of wavelengths is detected by the four linear array sensors 150A to 150D respectively.

As described above, in this embodiment, a collimated bundle of rays is split by dichroic mirrors arranged in the collimated bundle of rays. Because the distance between the two dichroic mirrors can be changed freely, the distance between the linear array sensors 150A and 150B for detecting the reflected light from the dichroic mirrors can be widened to about 50 mm easily. Further, because the linear array sensors 150C and 150D for detecting the transmitted light from the dichroic mirrors detect the transmitted light through the filters 110B and 110D located on the opposite sides of the filter set 110Y, the distance between the linear array sensors 150C and 150D can be widened.

Further, because the four right-angle prisms are replaced by the two dichroic mirrors, the number of constituent parts can be reduced compared with the first embodiment. As a result, the size of the system can be reduced.

Although the above description has been made about the case where the filters 110A to 110D are arranged between the lens 60 and the dichroic mirrors 160A and 160B, the invention may be applied also to the case where the filters 110A to 110D are arranged in the collimated bundle of rays between the dichroic mirrors 160A and 160B and the lenses 130A1 to 130B2. Further, the filter set 110A to 110D may be arranged in the position of the converged bundle of rays between the lenses 130A1 to 130B2 and the spacial filters 140A and 140B.

Further, the spacial filters (slits) are inserted in the front or rear of the lenses 130A1 to 130B2 or in the front or rear of the dichroic mirrors 160A and 160B if necessary.

Other features and modifications are equivalent to those in the embodiment shown in FIG. 2.

FIG. 6 is a configuration diagram of an optical system showing the configuration of the detector unit used in the multicolor fluorescence detection type electrophoretic analyzer according to a fourth embodiment of the present invention. The overall configuration of the multicolor fluorescence detection type electrophoretic analyzer according to this embodiment is the same as shown in FIG. 1.

Fluorescence emitted from each light-emitting point 80 is collected by the lens 60 and forms a collimated bundle of rays to be led to the detector unit 100C.

The detector unit 100C includes a filter set 110X, right-angle prisms 120A and 120B, lenses 130A1, 130A2, 130B1 and 130B2, spacial filters (slits) 140A and 140B, and four linear array sensors 150A to 150D.

After passing through the filter set 110X, the bundle of rays is partially bent perpendicularly by the two right-angle prisms 120A and 120B and partially moves straight so as to be split into four bundle of rays. That is, the optical system in this embodiment is designed so that one bundle of rays is split into four bundle of rays.

Light of the wavelength $\lambda 1$ selected by the filter 110A is reflected and bent perpendicularly by the right-angle prism 120A, and light of the wavelength $\lambda 2$ selected by the filter 110B is reflected and bent perpendicularly by the right-angle prism 120B. Further, light of the wavelength $\lambda 3$ selected by the filter 110C moves straight, and light of the wavelength $\lambda 4$ selected by the filter 110D moves straight. As described above, the optical system in this embodiment is designed so that one bundle of rays is split into four bundle of rays.

The four bundle of rays are converged by the lenses 130A1, 130A2, 130B1 and 130B2 so as to be focussed on light-receiving surfaces of the linear array sensors 150A to 150D respectively. That is, after light emitted from one light-emitting point 80 passes through the filters 110A to 110D so that four kinds of light of different wavelengths are selected by the filters 110A to 110D, fluorescent intensity corresponding to the four kinds of wavelengths is detected by the four linear array sensors 150A to 150D respectively. When, for example, five capillaries 10 are disposed parallelly to each other, each of the linear array sensors 150A to 150D has five light-receiving surfaces. The five light-receiving surfaces are arranged in the Z-axis direction (perpendicular to the plane of paper, that is, perpendicular to the X- and Y-axis directions). Accordingly, after light emitted from five light-emitting points in the five capillaries 10 passes through the filters 110A to 110D so that four kinds of light of different wavelengths are selected by the filters 110A to 110D, fluorescent intensity corresponding to the four kinds of wavelengths is detected by the respective five light-receiving surfaces on the four linear array sensors 150A to 150D.

As described above, in this embodiment, a collimated bundle of rays is split by two right-angle prisms arranged in the collimated bundle of rays. Because the distance between the two right-angle prisms can be changed freely, the distance between the linear array sensors 150A and 150B can be widened to about 50 mm easily. Further, because the linear array sensors 150C and 150D for detecting the straight moving light detect the transmitted light through the filters 110C and 110D located on the opposite sides of the filter set 110X, the distance between the linear array sensors 150C and 150D can be widened.

Further, because two right-angle prisms are removed consequently, the number of constituent parts can be reduced compared with the first embodiment. As a result, the size of the system can be reduced.

Other features and modifications in this embodiment are equivalent to those in the embodiment shown in FIG. 2.

FIG. 7 is a configuration diagram of an optical system showing the configuration of the detector unit used in the multicolor fluorescence detection type electrophoretic analyzer according to a fifth embodiment of the present invention. The overall configuration of the multicolor fluorescence detection type electrophoretic analyzer is the same as shown in FIG. 1.

Fluorescence emitted from each light-emitting point 80 is collected by the lens 60 and forms a collimated bundle of rays to be led to the detector unit 100D.

The detector unit 100D includes a filter set 110X, flat mirrors 170A and 170B, lenses 130A1, 130A2, 130B1 and 130B2, spacial filters (slits) 140A and 140B, and four linear array sensors 150A to 150D.

The filter set 110X has band-pass filters 110A, 110B, 110C and 110D for selecting four kinds of light of different wavelengths.

After passing through the filter set 110X, the bundle of rays is partially bent perpendicularly by the two flat mirrors 170A and 170B respectively and partially moves straight so as to be split into four bundle of rays. That is, the optical system in this embodiment is designed so that one bundle of rays is split into four bundle of rays.

Light of the wavelength $\lambda 1$ selected by the filter 110A is reflected and bent perpendicularly by the flat mirror 170A, and light of the wavelength $\lambda 2$ selected by the filter 110B is reflected and bent perpendicularly by the flat mirror 170B. Further, light of the wavelength $\lambda 3$ selected by the filter 110C moves straight, and light of the wavelength $\lambda 4$ selected by the filter 110D moves straight. As described above, the optical system in this embodiment is designed so that one bundle of rays is split into four bundle of rays.

The four bundle of rays are converged by the lenses 130A1, 130A2, 130B1 and 130B2 so as to be focussed on light-receiving surfaces of the linear array sensors 150A to 150D respectively. That is, after light emitted from the plurality of light-emitting points 80 passes through the filters 110A to 110D so that four kinds of light of different wavelengths are selected by the filters 110A to 110D, fluorescent intensity corresponding to the four kinds of wavelengths is detected by the four linear array sensors 150A to 150D respectively.

In this embodiment, a collimated bundle of rays is split by two flat mirrors arranged in the collimated bundle of rays. Because the distance between the two flat mirrors can be changed freely, the distance between the linear array sensors 150A and 150B can be widened to about 50 mm easily. Further, because the linear array sensors 150C and 150D for detecting the straight moving light detect the transmitted light through the filters 110C and 110D located on the opposite sides of the filter set 110X, the distance between the linear array sensors 150C and 150D can be widened.

Further, because the two flat mirrors are used, the number of constituent parts can be reduced compared with the first embodiment. As a result, the size of the system can be reduced. Further, because the flat mirrors are used, the system can be configured inexpensively.

Further, if the flat mirror 170A and the lens 130A1 are replaced by a concave mirror and the flat mirror 170B and the lens 130A2 are replaced by a concave mirror, the optical system can be more simplified.

Other features and modifications of this embodiment are equivalent to those in the embodiment shown in FIG. 2.

Although the above description has been made about the case where one bundle of rays is split into four bundle of rays, it may be said from another point of view that one bundle of rays is partially split and the optical axes of the thus split bundle of rays are separated spacially so that light intensity of the thus split bundle of rays is detected by the four linear array sensors individually.

Although the above description has been made about the case where the method for measuring fluorescence by radiation of excitation light in an electrophoretic medium as shown in FIG. 1 is used as means for enhancing the detection S/N, it is a matter of course that the optical system of the detector unit in each of the aforementioned embodiments can be applied also to a method for measuring fluorescence by radiation of excitation light in the outside of the electrophoretic medium, that is, capillary, by using a combination of sheath-flow techniques disclosed in U.S. Pat. No. 5,529,679.

Further, as means for selecting light of predetermined wavelengths, the band-pass filters may be replaced by interference filters.

What is claimed is:

1. A multicolor fluorescence detection type electrophoretic analyzer for separating a plurality of samples into sample components in a plurality of capillaries disposed in parallel to each other respectively by means of electrophoresis, radiating light from a light source onto said separated sample components in said capillaries in the manner that the light passes through the capillaries and measuring, by means of a detector unit, fluorescence emitted from said sample components, wherein said detector unit includes:

a condenser lens for collecting said fluorescence into a bundle of rays;

a splitter for splitting the bundle of rays collected by said condenser lens into a plurality of bundles of rays, including at least one optical device for turning a part of the bundle of rays from said condenser lens in a direction different from the direction of another part of the bundle of rays;

an optical filter set for filtering the split bundles of rays collected by said condenser lens to select light of different wavelengths; and a plurality of linear array sensors for detecting fluorescence which is emitted from said sample components separated in the plurality of capillaries and which has a wavelength selected by said optical filter set, correspondingly to each of said bundles of rays.

2. A multicolor fluorescence detection type electrophoretic analyzer according to claim 1, wherein portions corresponding to the plurality of capillaries, irradiated by light from said light source, are located straight.

3. A multicolor fluorescence detection type electrophoretic analyzer according to claim 1, further comprising a plurality of focusing lenses for focusing said bundle of rays on light-receiving portions of said linear array sensors.

4. A multicolor fluorescence detection type electrophoretic analyzer according to claim 1, wherein said optical device is constituted by at least one prism for reflecting a part of said bundle of rays.

5. A multicolor fluorescence detection type electrophoretic analyzer according to claim 4, wherein said prism is a right-angle prism for reflecting a part of said bundle of rays substantially perpendicularly.

6. A multicolor fluorescence detection type electrophoretic analyzer according to claim 1, wherein said optical device is constituted by at least one mirror for reflecting a part of said bundle of rays.

7. A multicolor fluorescence detection type electrophoretic analyzer according to claim 1, wherein said optical filter set is located between said condenser lens and said optical device.

8. A multicolor fluorescence detection type electrophoretic analyzer according to claim 7, wherein said optical filter set includes means for selecting wavelength of at least a portion of said bundle of rays incident to said optical device.

9. A multicolor fluorescence detection type electrophoretic analyzer according to claim 8, wherein said optical filter set is constituted by at least one dichroic mirror for reflecting light of a predetermined wavelength partially and transmitting light of another wavelength partially.

10. A multicolor fluorescence detection type electrophoretic analyzer for separating a plurality of samples into sample components in a plurality of capillaries disposed in parallel to each other respectively by means of electrophoresis, radiating light onto said separated sample components in said capillaries in the manner that the light passes through the capillaries and measuring, by means of a detector unit, fluorescence emitted from said sample components, wherein said detector unit includes:

a light collection means for collecting said fluorescence into a bundle of rays;

a luminous flux splitter means for splitting the bundle of rays collected by said light collection means into a plurality of bundles of rays including at least one optical device for turning a part of the bundle of rays from said condenser lens in a direction different from the direction of another part of the bundle of rays;

a wavelength selection means for filtering the split bundles of rays collected by said light collection means to select light of different wavelengths; and a plurality of linear array sensors for detecting fluorescence which is emitted from said plurality of capillaries and which has a wavelength selected by said wavelength selection means, correspondingly to each of said bundles of rays.

* * * * *